United States Patent [19]
Baltz et al.

[11] Patent Number: 5,821,098
[45] Date of Patent: Oct. 13, 1998

[54] GLYCOSYLTRANSFERASE GENE GTFD FROM *AMYCOLATOPSIS ORIENTALIS*

[75] Inventors: Richard H. Baltz; Patricia J. Solenberg, both of Indianapolis, Ind.

[73] Assignee: Eli Lilly and Company, Indianapolis, Ind.

[21] Appl. No.: 924,847

[21] Appl. No.:

[22] Filed: Sep. 5, 1997

Related U.S. Application Data

[60] Provisional application No. 60/026,028 Sep. 13, 1996.
[51] Int. Cl. [6] .......................... C12N 15/54; C12N 9/10; C12N 15/63; C12N 1/21
[52] U.S. Cl. .................. 435/193; 536/23.2; 435/172.3; 435/252.3; 435/252.33; 435/712; 435/74; 435/78
[58] Field of Search .................. 536/23.2; 435/172.3, 435/193, 252.3, 252.33, 71.2, 74, 78

[56] References Cited

PUBLICATIONS

S. K. Chung, et al. "Biosynthetic Studies f Aridicin Antibiotics: Microbial Transformations and Glycosylations by Protoplasts." *Journal of Antibiotics* 39(5):652–659 (May 1986).

M. J. Zmijewski, Jr., and B. Briggs. "Biosynthesis of vancomycin: identification of TDP–glucose: aglycosyl–vancomycin glucosyltransferase from *Amycolatopsis orientalis*." *FEMS Microbiology Letters* 5:129–134 (1989).

M. J. Zmijkjewski, Jr., and J. T. Fayerman. *Genetics and Biochemistry of Antibiotic Production* Ed. L.C. Vining and C. Stuttard. Butterworth Heinemann, Boston. Chapter 18: "Glycopeptide Antibiotics."pp. 71–83 (1985).

*Primary Examiner*—Rebecca E. Prouty
*Attorney, Agent, or Firm*—Thomas D. Webster; David E. Boone

[57] ABSTRACT

The invention provides isolated nucleic acid compounds encoding the glycosyltransferase protein GtfD of *Amycolatopsis orientalis*. Also provided are vectors carrying the gtfD gene, transformed heterologous host cells for expressing the GtfD protein, and methods for producing glycopeptide compounds using the cloned gtfD gene.

10 Claims, No Drawings

GLYCOSYLTRANSFERASE GENE GTFD FROM *AMYCOLATOPSIS ORIENTALIS*

This application claims the benefit of provisional application 60/026,028, filed Sep. 13, 1996, now abandoned.

BACKGROUND OF THE INVENTION

This invention relates to recombinant DNA technology. In particular the invention pertains to the cloning of glycosyltransferase gene gtfD from *Amycolatopsis orientalis*, the use of the cloned gene to express and purify the encoded enzyme, and the use of the cloned enzyme in the in vitro production of glycopeptide compounds.

The use of antibiotic compounds has had a profound impact on the practice of medicine in the United States and around the world. Two highly effective antibiotic compounds of the glycopeptide class, vancomycin and teichoplanin, have been approved for use in humans.

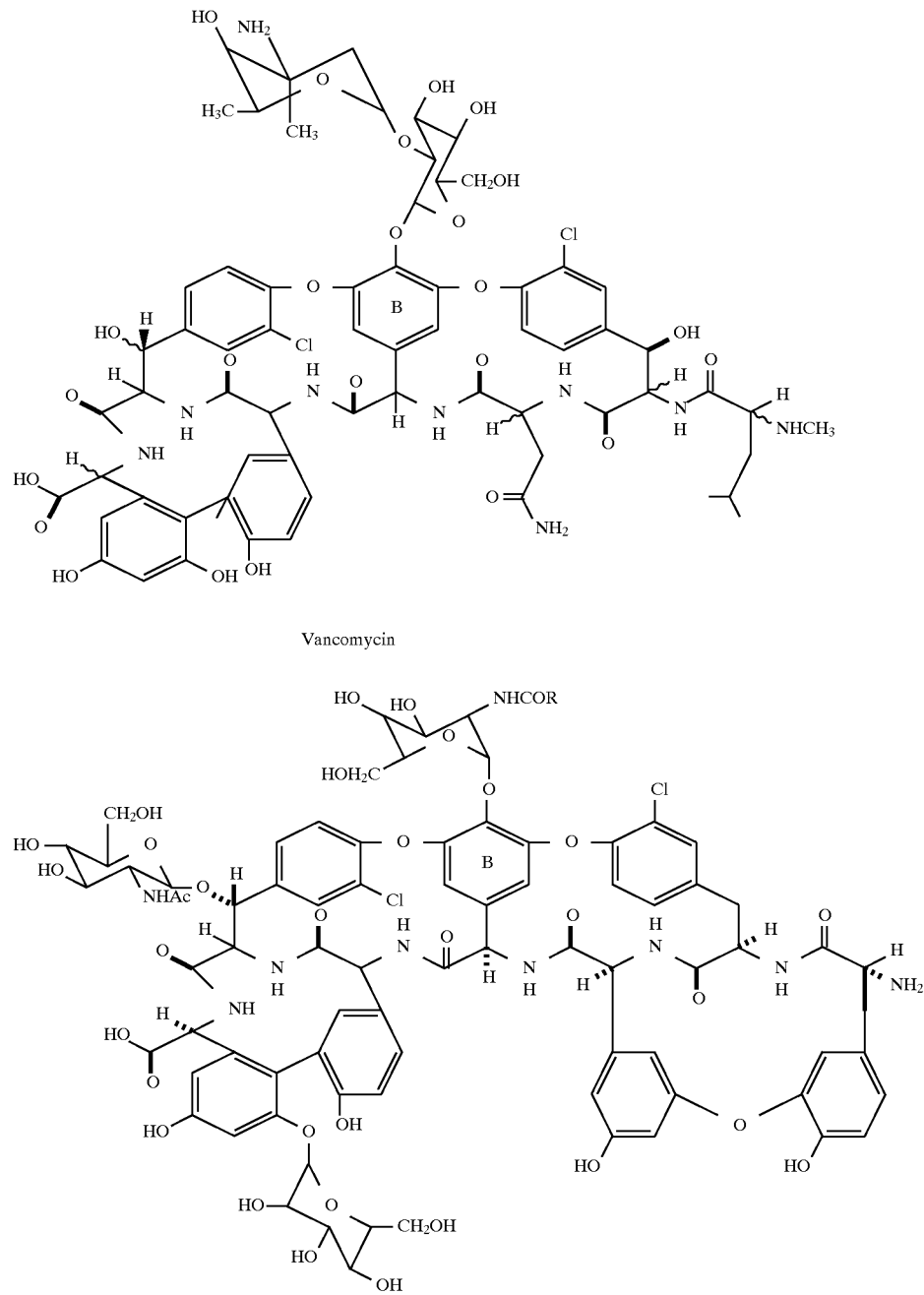

Vancomycin

Teicoplanin: R = 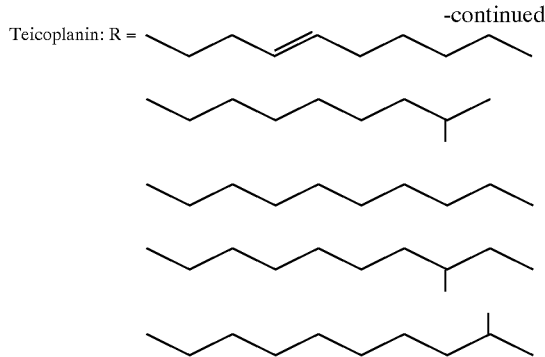
-continued

The glycopeptide antibiotics comprise natural and semi-synthetic compounds of highly functionalized linear heptapeptides having a core structure composed of either seven modified or unusual aromatic amino acids, or a mix of aromatic and aliphatic amino acids. Natural glycopeptide compounds have been found in a variety of bacterial genera including Streptomyces, Actinoplanes, Nocardia, Amycolatopsis, Kibdelosporangia, and Pseudonocardia. M. Zmijewski and J. Fayerman. "Glycopeptide Antibiotics," In *Genetics and Biochemistry of Antibiotic Production,* Chap. 18. Ed. L. C. Vining and C. Studtard. Publ. Butterworth Heinemann, Boston (1995). Generally, glycopeptide compounds are differentiated by the placement of sugar substituents on the peptide core. In some instances differentiation arises from the positioning of fatty acid moieties on the sugar substituents. Research has shown that the sugar moieties attached to the core have an effect on the biological activity of glycopeptide molecules.

At present, investigations into glycosylation of glycopeptides and glycopeptide cores are limited to preliminary observations on crude cellular extracts of bacterial strains that produce glycopeptide compounds. These experiments have demonstrated that the glycosylation reaction appears to involve one or more enzymatic activities which attach sugar residues onto a glycopeptide core. One study, for example, demonstrated a glycosylating activity in a crude cellular extract of a vancomycin-producing strain of *Amycolatopsis orientalis.* M. Zmijewski & B. Briggs. "Biosynthesis of vancomycin: identification of TDP-glucose:aglycosylvancomycin glucosyltransferase from *Amycolatopsis orientalis*" FEMS Microbiol. Lett. 59, 129–134 (1989).

The glycosylation of glycopeptide compounds, intrinsically interesting from a scientific point of view, presents a number of practical considerations that warrant continued study of this subject. Recently, a number of glycopeptide resistant strains of pathogenic organisms have been encountered within the clinical environment. This trend toward diminished efficacy of glycopeptide compounds is alarming because of a similar phenomenon in the case of β-lactam antibiotics. It is clear that the rise in antibiotic resistance has occured by a plurality of molecular mechanisms and that resistant organisms possess a diverse repertoire for counteracting the otherwise lethal effect of antibiotic compounds.

In light of the trend toward greater resistance, and in view of the absence of effective alternative treatments, there exists a pressing need to develop new antibiotic compounds. A useful strategy toward this end involves derivitizing presently available glycopeptide compounds by engineering in defined ways the placement and configuration of sugar moieties on the glycopeptide core structure. Achieving molecular rearrangements and substitutions on glycopeptide compounds by chemical means is difficult if not impossible in most cases. By contrast to chemical procedures, enzymatic methods, if available, would provide an effective means to engineer specific modifications onto the glycopeptide core.

The challenge to provide an enzymatic means for modifying glycopeptide core molecules has been met by the present invention. Described herein are gtfD genes isolated from *Amycolatopsis orientalis* encoding glycosyltransferase enzyme GtfD, which adds vancosamine onto the glucose moiety of desvancosaminyl vancomycin.

BRIEF SUMMARY

The present invention is designed to meet the aforementioned need and provides, inter alia, the isolated gtfD gene and other nucleic acid molecules that encode the GtfD gene product from *Amycolatopsis orientalis.* The invention also provides the GtfD protein product of the *Amycolatopsis orientalis* gtfD gene, in substantially purified form.

Having the cloned gtfD gene of *Amycolatopsis orientalis* enables the production of recombinant GtfD protein from which can be made derivatives of glycopeptide compounds in vitro.

In one embodiment the present invention relates to an isolated DNA molecule encoding GtfD protein, said DNA molecule comprising the nucleotide sequence identified as SEQ ID NO. 1: ATGCGTGTGT TGTTGTCGGT GTGCG-GAACC CGCGGGACG TCGAGATCGC GGT-GTCGCTG 60 GCGGTCCGGC TGAAGGCGCT CGGCGTCGGG ACGCGGATGT GCGCACCGCC CGC-CGCCGCC 120 GAGCGGCTGG CCGAGGTCGA GGT-GCCGCAT GTGCCGGTCG GCCTTCCGCA GCACAT-GATG 180 TTGCAGGAGG GGATGCCGCC GCCGCCCCCG GAGGAGGAGC GGCGGCTCGC GGC-CATGACG 240 GTCGAGATGC AGTTCGACGC GATC-CCCTCG GCCGCCGAAG GATGCGTGGC GGTGGTG-GCG 300 GTCGGCGATC TGGCCGCCGC GACCGGCGTG CGGTCGGTGG CCGAAAAGCT GGGCCTCCCC 360
TTCTTCTACT CCGTCCCGAG CCCGGTCTAC CTGGCTTCCC CGCACTTCCC GCCGCCCTAT 420
GACGAGCCGA CCACCCCGGG CGTGACCGAC CACCGGACAC TGTGGGAAGA GCGTGCCCAC 480
CGGTTCGCGG AACGGTACGG GGAGACGCTC AACCGGCGGC GGGCCGCGAT CGGCCTGCCG 540
CCGGTGGAGG ACGTCTTCGG CTACGGCCAC GGCGACCGGC CCATCCTGTC GGCGGACCCG 600
GTCCTCGCCC CGCTGCAGCC GGACGTCGAC GCCGTGCAGA CCGGCGCGTG GATCCTGACC 660
GACGACCGGC CGCTTCCCCC GGAGCTGGAG GCGTTCCTGG CCGCCGGCCC ACCGCCGGTG 720
CACGTGGGTT TCGGCAGCTC GTCCGGGAAG GGGATCGCCG ACGCCGCGAA GATCGCCGTC 780
GAGGTGAGCC GTGCCCACGG CCGCCGGGTG ATCCTCTCCC GAGGGTGGAC 5 CGATCTGCTC 840 CTGCCCGACG ACCGGGAGGA CTGTTTCGCC ATCGGCGAGG TGAACTTCCA GGCGCTGTTC 900
CCCCGGGTGG CCGCCGTCAT CCATCACGGC AGCGCGGGCA CGGAACACGT GGCCACGCGG 960
GCGGGCGTCC CCCAGCTCGT GATCCCCCGG AACACCGACC AGCCGTACTT CGCCGCCAGG 1020
GTTGCCGATC TGGGGATCGG TGTGGCGCAC GACGGCCCGA CGCCGACCTT CGAGTCCCTG 1080
TCGGCCGCGC TCACCACGGT CCTGGCGCCG GAAACGCGCG CGCGGGCGCG GGCCGTGGCG 1140
GCCATGGCCC AGACCGACGG CGCGGCGGCG GCCGCGGATC TGGTGCTCGC CGCCGTCGGC 1200
GGGAACGAGC CCGCCGTTCC CGCG 1224

In another embodiment the present invention relates to a glycosyltransferase protein molecule, encoded by SEQ ID NO:1 wherein said glycosyltransferase protein molecule comprises the sequence identified as SEQ ID NO. 2.

In a further embodiment the present invention relates to a ribonucleic acid molecule encoding GtfD protein, said ribonucleic acid molecule comprising the sequence identified as SEQ ID NO. 3:

In yet another embodiment, the present invention relates to a recombinant DNA vector which incorporates the *Amycolatopsis orientalis* gtfD gene in operable linkage to gene expression sequences enabling the gtfD gene to be transcribed and translated in a host cell.

In still another embodiment the present invention relates to homologous or heterologous host cells which have been transformed or transfected with the cloned gtfD gene of *Amycolatopsis orientalis* such that the gtfD gene is expressed in the host cell.

In still another embodiment the present invention relates to a method for producing glycopeptide compounds wherein recombinantly produced GtfD protein is utilized to add one or more sugar moieties onto a glycopeptide.

In a further embodiment the present invention relates to vancomycin which is produced in vitro using recombinant GtfD protein to glycosylate desvancosaminyl vancomycin.

DEFINITIONS

"AGV" denotes aglycosylvancomycin which comprises a vancomycin core having a free hydroxl group on the B ring in place of the disaccharide moiety.

"DVV" denotes desvancosaminyl vancomycin in which a glucose residue is attached onto AGV at the free hydroxl position of the B ring.

The terms "cleavage" or "restriction" of DNA refers to the catalytic cleavage of the DNA with a restriction enzyme that acts only at certain sequences in the DNA (viz. sequence-specific endonucleases). The various restriction enzymes used herein are commercially available and their reaction conditions, cofactors, and other requirements are used in the manner well known to one of ordinary skill in the art. Appropriate buffers and substrate amounts for particular restriction enzymes are specified by the manufacturer or can readily be found in the literature.

The term "fusion protein" denotes a hybrid protein molecule not found in nature comprising a translational fusion or enzymatic fusion in which two or more different proteins or fragments thereof are covalently linked on a single polypeptide chain.

The term "plasmid" refers to an extrachromosomal genetic element. The starting plasmids herein are either commercially available, publicly available on an unrestricted basis, or can be constructed from available plasmids in accordance with published procedures. In addition, equivalent plasmids to those described are known in the art and will be apparent to the ordinarily skilled artisan.

"Recombinant DNA cloning vector" as used herein refers to any autonomously replicating agent, including, but not limited to, plasmids and phages, comprising a DNA molecule to which one or more additional DNA segments can or have been added.

The term "recombinant DNA expression vector" as used herein refers to any recombinant DNA cloning vector, for example a plasmid or phage, in which a promoter and other regulatory elements are present to enable transcription of the inserted DNA.

The term "vector" as used herein refers to a nucleic acid compound used for introducing exogenous DNA into host cells. A vector comprises a nucleotide sequence which may encode one or more protein molecules. Plasmids, cosmids, viruses, and bacteriophages, in the natural state or which have undergone recombinant engineering, are examples of commonly used vectors.

The terms "complementary" or "complementarity" as used herein refers to the capacity of purine and pyrimidine nucleotides to associate through hydrogen bonding in double stranded nucleic acid molecules. The following base pairs are complementary: guanine and cytosine; adenine and thymine; and adenine and uracil.

The term "glycopeptide" refers to a functionalized linear heptapeptide compound of natural or semi-synthetic origin, said compound having a core structure.

"Glycopeptide core" or "core" or "core compound" interchangeably denote the progenitor structure of all glycopeptide compounds, comprising either 7 modified or unusual aromatic amino acids, or a mix of aromatic and aliphatic amino acids.

"Glycosylating substrate" refers to a compound which functions as a donor of a sugar moiety in an enzymatic glycosylation reaction, for example, uridine diphosphate-D-glucose.

"Isolated nucleic acid compound" refers to any RNA or DNA sequence, however constructed or synthesized, which is locationally distinct from its natural location.

A "primer" is a nucleic acid fragment which functions as an initiating substrate for enzymatic or synthetic elongation of, for example, a nucleic acid molecule.

The term "promoter" refers to a DNA sequence which directs transcription of DNA to RNA.

A "probe" as used herein is a labeled nucleic acid compound which hybridizes with another nucleic acid compound.

The term "hybridization" as used herein refers to a process in which two or more strands of nucleic acid join through base pairing with complementary strands. "Selective hybridization" refers to hybridization under conditions of high stringency. The degree of hybridization between nucleic acid molecules varies with the degree of complementarity, the stringency of the hybridization conditions, and the length of the strands.

The term "stringency" refers to a set of hybridization conditions, for example temperature and salt concentration, which may be varied to achieve "high stringency" or "low stringency" conditions, thereby varying the degree of hybridization of one nucleic acid molecule with another nucleic acid molecule. High stringency conditions disfavor non-homologous basepairing.

DETAILED DESCRIPTION

The gtfD gene of Amycolatopsis orientalis encodes a glycosylating enzyme, GtfD. The enzyme will add vancosamine onto the glucose residue of desvancosaminyl vancomycin (DVV) forming vancomycin. The enzyme uses TDP-vancosamine, or UDP-vancosamine as the glycosylating substrate.

The gtfD gene of *Amycolatopsis orientalis* comprises a DNA sequence of 1224 nucleotide base pairs (SEQ ID NO. 1). There are no intervening sequences. Those skilled in the art will recognize that owing to the degeneracy of the genetic code (i.e. 64 codons which encode 20 amino acids), numerous "silent" substitutions of nucleotide base pairs could be introduced into the sequence identified as SEQ ID NO. 1 without altering the identity of the encoded amino acid(s) or protein product identified as SEQ ID NO:2. All such substitutions are intended to be within the scope of the invention.

Gene Isolation Procedures

Those skilled in the art will recogize that the gtfD gene may be obtained by a plurality of applicable techniques including, for example, polymerase chain reaction (PCR) amplification, or de novo DNA synthesis.(See e.g., J. Sambrook et al. *Molecular Cloning,* 2d Ed. Chap. 14 (1989)).

Methods for constructing gene libraries in a suitable vector such as a plasmid or phage for propagation in procaryotic or eucaryotic cells are well known to those skilled in the art. [See e.g. J. Sambrook et al. Supra]. Suitable cloning vectors are widely available.

Skilled artisans will recognize that the gtfD gene of *Amycolatopsis orientalis* or fragment thereof could also be isolated by PCR amplification of *Amycolatopsis orientalis* genomic DNA using oligonucleotide primers targeted to any suitable region of SEQ ID NO. 1. Methods for PCR amplification are widely known in the art. See e.g. *PCR Protocols: A Guide to Method and Application,* Ed. M. Innis et al., Academic Press (1990), which hereby is incorporated by reference. The PCR amplification, which comprises genomic DNA, suitable enzymes, primers, and buffers, is conveniently carried out in a DNA Thermal Cycler (Perkin Elmer Cetus, Norwalk, Conn.). A positive PCR amplification is determined by detecting an appropriately-sized DNA fragment following agarose gel electrophoresis.

Protein Production Methods

One embodiment of the present invention relates to the substantially purified protein GtfD identified as SEQ ID NO:2 and encoded by the gtfD gene or functionally related proteins of *Amycolatopsis orientalis.*

Skilled artisans will recognize that the proteins of the present invention can be synthesized or purified by any number of suitable methods. For example, the amino acid compounds of the invention can be made by chemical methods well known in the art, including solid phase peptide synthesis or recombinant methods. Both methods are described in U.S. Pat. No. 4,617,149, incorporated herein by reference.

The principles of solid phase chemical synthesis of polypeptides are well known in the art and are described in a number of general texts on the subject. See, e.g., H. Dugas and C. Penney, *Bioorganic Chemistry* (1981) Springer-Verlag, New York, 54–92. For example, peptides may be synthesized by solid-phase methodology using an Applied Biosystems 430A peptide synthesizer (Applied Biosystems, Foster City, Calif.) and synthesis cycles supplied by Applied Biosystems. Protected amino acids, such as t-butoxycarbonyl-protected amino acids, and other reagents are commercially available from many chemical supply houses.

Sequential t-butoxycarbonyl chemistry using double-couple protocols are applied to the starting p-methyl benzhydryl amine resins for the production of C-terminal carboxamides. For the production of C-terminal acids, the corresponding pyridine-2-aldoxime methiodide resin is used. Asparagine, glutamine, and arginine are coupled using preformed hydroxy benzotriazole esters. Following completion of the synthesis the peptides may be deprotected and cleaved from the resin with anhydrous hydrogen fluoride containing 10% meta-cresol. Cleavage of the side chain protecting group(s) and of the peptide from the resin is carried out at zero degrees Celcius or below, preferably −20_for thirty minutes followed by thirty minutes at 0_C.

The proteins of the present invention can also be produced by recombinant DNA methods using the cloned gtfD gene of *Amycolatopsis orientalis*. Recombinant methods are preferred if a high yield is desired. Expression of the cloned gtfD gene can be carried out in a variety of suitable host cells well known to those skilled in the art. The gtfD gene is introduced into a host cell by any suitable transformation, transfection, or conjugation means, well known to those skilled in the art. While chromosomal integration of the cloned gtfD gene is within the scope of the present invention, it is preferred that the gene be cloned into a suitable extra-chromosomally maintained expression vector so that the coding region of the gtfD gene is operably linked to a constitutive or inducible promoter.

The basic steps in the recombinant production of the GtfD protein are:

a) constructing a natural, synthetic or semi-synthetic DNA encoding GtfD protein;

b) integrating said DNA into an expression vector in a manner suitable for expressing the GtfD protein, either alone or as a fusion protein;

c) transforming, transfecting, or otherwise introducting said expression vector into an appropriate eukaryotic or prokaryotic host cell to form a recombinant host cell, d) culturing said recombinant host cell under conditions that favor expression of the GtfD protein; and e) recovering and purifying the GtfD protein by any suitable means.

Expressing Recombinant GtfD Protein in Procaryotic and Eucaryotic Host Cells

In general, prokaryotes are used for cloning DNA and for constructing the vectors of the present invention. Prokaryotes are also employed in the production of the GtfD protein. For example, the *Escherichia coli* K12 strain 294 (ATCC No. 31446) is particularly useful for the expression of foreign proteins. Other strains of *E. coli,* bacilli such as *Bacillus subtilis,* enterobacteriaceae such as *Salmonella typhimurium* or *Serratia marcescans,* various Pseudomonas species, and other bacteria, such as Streptomyces, may also be employed as host cells in the cloning and expression of the recombinant proteins of this invention.

Promoters suitable for driving the expression of gene sequences in prokaryotes include β-lactamase [e.g. vector pGX2907, ATCC 39344, contains a replicon and β-lactamase gene], lactose systems [Chang et al., Nature (London), 275:615 (1978); Goeddel et al., Nature (London), 281:544 (1979)], alkaline phosphatase, and the tryptophan (trp) promoter system [vector PATHI (ATCC 37695) which is designed to facilitate expression of an open reading frame as a trpE fusion protein under the control of the trp promoter]. Hybrid promoters such as the tac promoter (isolatable from plasmid pDR540, ATCC-37282) are also suitable. Still other bacterial promoters, whose nucleotide sequences are generally known, enable one of skill in the art to ligate such promoter sequences to DNA encoding the proteins of the instant invention using linkers or adapters to supply any required restriction sites. Promoters for use in bacterial systems also will contain a Shine-Dalgarno sequence operably linked to the DNA encoding the desired polypeptides. These examples are illustrative rather than limiting.

The protein of this invention may be synthesized by recombinant or chemical means as the amino acid sequence identified as SEQ ID NO:2, or as a fusion protein comprising the protein of interest and another protein or peptide which may be removable by enzymatic or chemical cleavage. Expression as a fusion protein may prolong the lifespan, increase the yield of the desired peptide, or provide a convenient means for purifying the protein. A variety of peptidases (e.g. enterokinase and thrombin) which cleave a polypeptide at specific sites are known. Furthermore, particular chemicals (e.g. cyanogen bromide) will cleave a polypeptide chain at specific sites. The skilled artisan will appreciate the modifications necessary to the amino acid sequence (and synthetic or semi-synthetic coding sequence if recombinant means are employed) to incorporate site-specific internal cleavage sites. See e.g., P. Carter, "Site Specific Proteolysis of Fusion Proteins", Chapter 13, in *Protein Purification: From Molecular Mechanisms to Large Scale Processes,* American Chemical Society, Washington, D.C. (1990).

In addition to prokaryotes, mammalian host cells and eukaryotic microbes such as yeast may also be used to isolate and express the genes of the present invention. The simple eucaryote *Saccharomyces cerevisiae,* is the most commonly used eukaryotic microorganism, although a number of other yeasts such as *Kluyveromyces lactis* are also suitable. For expression in Saccharomyces, the plasmid YRp7 (ATCC-40053), for example, may be used. See, e.g., L. Stinchcomb, et al., Nature, 282:39 (1979); J. Kingsman et al., Gene, 7:141 (1979); S. Tschemper et al., Gene, 10:157 (1980). Plasmid YRp7 contains the TRP1 gene which provides a selectable marker for use in a trp1 auxotrophic mutant.

Purification of Recombinantly-Produced GtfD Protein

An expression vector carrying the cloned gtfD gene of *Amycolatopsis orientalis* is transformed, transfected, or otherwise introduced into a suitable host cell using standard methods. Cells which contain the vector are propagated under conditions suitable for expression of the Glycosyltransferase protein. If the gtfD gene is under the control of an inducible promoter, growth media and other conditions should incorporate the appropriate inducer.

The recombinantly produced protein may be purified from cellular extracts of transformed cells by any suitable means. In a preferred protein purification method, the gtfD gene is modified at the 5' end to incorporate several histidine residues at the amino terminus of the GtfD protein product. The "histidine tag" enables a single-step protein purification method referred to as "immobilized metal ion affinity chromatography" (IMAC), essentially as described in M. C. Smith et al. "Chelating Peptide-immobilized metal-ion affinity chromatography," Chapter 12, in *Protein Purification: From Molecular Mechanisms to Large Scale Processes,* American Chemical Society, Washington, D.C. (1990), and in U.S. Pat. No. 4,569,794 both of which hereby are incorporated by reference. The IMAC method enables rapid isolation of substantially pure protein.

The gtfD gene, which comprises nucleic acid encoding SEQ ID NO:2, may also be produced using synthetic methodology. The synthesis of nucleic acids is well known in the art. See, e.g., E. L. Brown, R. Belagaje, M. J. Ryan, and H. G. Khorana, *Methods in Enzymology,* 68:109–151 (1979). The DNA segments corresponding to the gtfD gene could be generated using a conventional DNA synthesizing apparatus, such as the Applied Biosystems Model 380A or 380B DNA synthesizers (Applied Biosystems, Inc., 850 Lincoln Center Drive, Foster City, Calif. 94404) which employ phosphoramidite chemistry. Alternatively, phosphotriester chemistry may be employed to synthesize the nucleic acids of this invention. [See, e.g., M. J. Gait, ed., *Oligonucleotide Synthesis, A Practical Approach,* (1984).]

The ribonucleic acids of the present invention may be prepared using the polynucleotide synthetic methods discussed supra, or they may be prepared enzymatically using RNA polymerases to transcribe a DNA template.

The most preferred systems for preparing the ribonucleic acids of the present invention employ the RNA polymerase from the bacteriophage T7 or the bacteriophage SP6. These RNA polymerases are highly specific and require the insertion of bacteriophage-specific sequences at the 5' end of the template to be transcribed. See, J. Sambrook, et al., supra, at 18.82–18.84.

This invention also provides nucleic acids, RNA or DNA, which are complementary to SEQ ID NO:1 or SEQ ID NO:3.

The present invention also provides probes and primers useful for a variety of molecular biology techniques. For example, the nucleic acid compounds of the present invention may be used to hybridize to genomic DNA which has been digested with one or more restriction enzymes and separated on an electrophoretic gel. The hybridization of radiolabeled probes onto such restricted DNA, usually fixed to a membrane after electrophoresis, is well known in the art. See, e.g., J. Sambrook, supra. A compound which comprises SEQ ID NO:1, SEQ ID NO:3 or a complementary sequence of SEQ ID NO:1 or SEQ ID NO:3, or a fragment thereof, and which is at least 18 base pairs in length, and which will selectively hybridize to *Amycolatopsis orientalis* DNA or mRNA encoding gtfD, is provided. Preferably, the 18 or more base pair compound is DNA. The probes and primers of this invention can be prepared by techniques well known to those skilled in the art (See e.g. Sambrook et al. supra). In a most preferred embodiment these probes and primers are synthesized using chemical means as described above.

Another aspect of the present invention relates to recombinant DNA cloning vectors and expression vectors comprising the nucleic acids of the present invention. Many of the vectors encompassed within this invention are described above. The preferred nucleic acid vectors are those which comprise DNA. The most preferred recombinant DNA vectors comprise the isolated DNA sequence, SEQ ID NO:1. Plasmid pCZA366 is an especially preferred DNA vector of the present invention.

Choosing the most appropriate cloning vector or expression vector depends upon a number of factors including the availability of appropriate restriction enzyme sites, the type of host cell into which the vector is to be transfected or transformed, the purpose of the transfection or transformation (e.g., stable transformation as an extrachromosomal element, or integration into the host chromosome), the presence or absence of readily assayable or selectable markers (e.g., antibiotic resistance markers and metabolic markers), and the desired number of copies of the gene to be present in the host cell.

Vectors suitable to carry the nucleic acids of the present invention comprise RNA viruses, DNA viruses, lytic bacteriophages, lysogenic bacteriophages, stable bacteriophages, plasmids, viroids, and the like. The most preferred vectors are plasmids.

When preparing an expression vector the skilled artisan understands that there are many variables to be considered, for example, whether to use a constitutive or inducible promoter. Inducible promoters are preferred because they enable high level, regulatable expression of an operably linked gene. A number of inducible promoters responding to a variety of induction signals are available, for example, carbon source, metal ions, and heat. The practitioner also understands that the amount of nucleic acid or protein to be produced dictates, in part, the selection of the expression system. The addition of certain nucleotide sequences, such as a sequence encoding a signal peptide preceding the coding sequence, is useful to direct localization of the resulting polypeptide.

Host cells harboring the nucleic acids disclosed herein are also provided by the present invention. A preferred host is *E. coli* which has been transfected or transformed with a vector which comprises a nucleic acid of the present invention.

The present invention also provides a method for constructing a recombinant host cell capable of expressing SEQ ID NO:2, said method comprising transforming or otherwise introducing into a host cell a recombinant DNA vector that comprises an isolated DNA sequence which encodes SEQ ID NO:2. A preferred host cell is any strain of *E. coli* which can accomodate high level expression of a gene(s) introduced by transformation or transfection. Preferred vectors for expression are those which comprise SEQ ID NO:1. An especially preferred expression vector for use in *E. coli* is plasmid pCZA366, which comprises SEQ ID NO:1. Transformed host cells may be cultured under conditions well known to skilled artisans such that SEQ ID NO:2 is expressed, thereby producing GtfD protein in the recombinant host cell.

The cloned GtfD enzyme is useful for glycosylating glycopeptide compounds in vitro. A method embodied herein comprises glycosylating a glycopeptide compound by contacting the glycopeptide with the cloned GtfD protein and monitoring the glycopeptide compound that is produced.

The instant invention provides an enzymatic method for the in vitro glycosylation of DVV using the cloned *A. orientalis* gtfD gene, said method comprising the steps of:
a) expressing the cloned gtfD gene in a host cell so that GtfD enzyme is produced;
b) exposing said GtfD enzyme to a glycopeptide compound, in vivo or in vitro;

c) introducing a suitable glycosylating substrate; and d) characterizing and/or purifying the product glycopeptide by any suitable means.

The method can be adapted to substantially purified recombinant GtfD protein, as described herein, or to a crude cellular extract isolated from a recombinant cell culture that expresses the GtfD protein by virtue of having been transformed, transfected, or otherwise endowed with the gtfD gene.

A suitable substrate for the in vitro glycosylation reaction comprises TDP-vancosamine. This substrate can be obtained by acid-catalyzed hydrolysis of vancomycin using any suitable method known to skilled artisans (See e.g. M. Sim et al. "Synthesis and use of glycosyl phosphites: an effective route to glycosyl phophates, sugar nucleotides, and glycosides" J. Am. Chem. Soc. 115, 2260–67 (1993)). In one method for preparation of this substrate, following acid hydrolysis of vancomycin, the hydrolytic products are condensed with dibenzyl N,N-diethylphosphoramidite as a phosphitylating reagent so as to generate the appropriate dibenzyl glycosyl phosphite derivative. Oxidation and deprotection, followed by reaction with thymidine 5'-monophospho-morpholidate provides the desired sugar substrate.

The following examples more fully describe the present invention. Those skilled in the art will recognize that the particular reagents, equipment, and procedures described are merely illustrative-and are not intended to limit the present invention in any manner.

EXAMPLE 1

Construction of a DNA Vector for Expressing *Amycolatoosis orientalis* Gene gtfD in *Escherichia coli*

Plasmid pCZA366 is an approximately 7 kilobasepair expression vector suitable for expressing the gtfD gene at high levels in a procaryotic host, for example *E. coli.* Plasmid pCZA366 is derived from parent plasmid PET-la (obtained from Novagen, Madison, Wis.), which contains an origin of DNA replication (ori), an ampicillin resistance gene (Amp), the T7 promoter region, and the laci gene for repressing the lac operon.

The gtfD gene cassette inserted into pCZA366 is generated by the PCR carried out on *A. orientalis* C329.4 genomic DNA using standard conditions. Primers used in the amplification reaction are complementary to the 5' and 3' ends of the gtfD gene sequence specified in SEQ ID NO: 1 and are engineered to contain NdeI and BglII restriction sites. The PCR-amplified gtfD gene sequence is digested with NdeI and BglII and ligated into pET11a, which has been digested with NdeI and BamHI.

EXAMPLE 2

Transformation of Escherichia coli with an Expression Plasmid Carrying the gtfD gene of *Amycolatoosis orientalis*

Plasmid pCZA366 is transformed into *E. coli* BL21(DE3) (hsdS gal λcIts857 ind1Sam7nin5lacUV5-T7gene 1) using standard methods (See e.g. Sambrook et al. Supra).

EXAMPLE 3

In Vitro Glycosylation of Desvancosaminyl Vancomycin Using Cloned qtfD Gene

Approximately 25 ml of a culture of *E. coli* BL21(DE3) cells transformed with plasmid pCZA366 is grown to an $OD_{600}$ of about 0.6. Induction of gtfD gene expression is effected by adding 1 mM IPTG with shaking at room temperature for 2 to 3 hours. Thereafter, cells from about 20 ml of the induced culture are pelleted by centrifugation and resuspended in 2 ml of 50 mM Tris pH 9.0, 100 μg/ml lysozyme with incubation on ice for 10 minutes to effect cell lysis. After cell lysis the suspension is passed through a 23-gauge syringe and centrifuged at 10,000 x g for 15 minutes to pellet cell debris. The resulting cell extract is used for the glycosylation reaction.

The 1 ml glycosylation reaction contained:
1 mg DVV in 50 mM Tris HCL, pH 9.0
5 mg TDP-vancosamine
1 mg bovine serum albumin (BSA)
20 µl 1M MgCl2
20 µl 1M CaCl2
5 µl 1M dithiothreitol (DTT)
445 µl cell extract
Distilled water to 1 ml.

A control reaction contained cell extract from non-transformed BL21(DE3). After incubation overnight at 37_C with slight shaking the reaction is filtered through a 0.45 micron filter and analyzed by HPLC.

---

We claim:
1. An isolated nucleic acid compound encoding the protein having the amino acid sequence which is SEQ ID NO 2.
2. An isolated nucleic acid compound comprising a sequence encoding the protein of SEQ ID NO:2 wherein said compound has a sequence selected from the group consisting of:
(a) ATGCGTGTGT TGTTGTCGGT GTGCGGAACC CGCGGGGACG TCGAGATCGC GGTGTCGCTG 60
GCGGTCCGGC TGAAGGCGCT CGGCGTCGGG ACGCGGATGT GCGCACCGCC CGCCGCCGCC 120
GAGCGGCTGG CCGAGGTCGA GGTGCCGCAT GTGCCGGTCG GCCTTCCGCA GCACATGATG 180
TTGCAGGAGG GGATGCCGCC GCCGCCCCCG GAGGAGGAGC GGCGGCTCGC GGCCATGACG 240
GTCGAGATGC AGTTCGACGC GATCCCCTCG GCCGCCGAAG GATGCGTGGC GGTGGTGGCG 300
GTCGGCGATC TGGCCGCCGC GACCGGCGTG CGGTCGGTGG CCGAAAAGCT GGGCCTCCCC 360
TTCTTCTACT CCGTCCCGAG CCCGGTCTAC CTGGCTTCCC CGCACTTCCC GCCGCCCTAT 420
GACGAGCCGA CCACCCCGGG CGTGACCGAC CACCGGACAC TGTGGGAAGA GCGTGCCCAC 480
CGGTTCGCGG AACGGTACGG GGAGACGCTC AACCGGCGGC GGGCCGCGAT CGGCCTGCCG 540
CCGGTGGAGG ACGTCTTCGG CTACGGCCAC GGCGACCGGC CCATCCTGTC GGCGGACCCG 600
GTCCTCGCCC CGCTGCAGCC GGACGTCGAC GCCGTGCAGA CCGGCGCGTG GATCCTGACC 660
GACGACCGGC CGCTTCCCCC GGAGCTGGAG GCGTTCCTGG CCGCCGGCCC ACCGCCGGTG 720
CACGTGGGTT TCGGCAGCTC GTCCGGGAAG GGGATCGCCG ACGCCGCGAA GATCGCCGTC 780
GAGGTGAGCC GTGCCCACGG CCGCCGGGTG ATCCTCTCCC GAGGGTGGAC CGATCTGCTC 840
CTGCCCGACG ACCGGGAGGA CTGTTTCGCC ATCGGCGAGG TGAACTTCCA GGCGCTGTTC 900
CCCCGGGTGG CCGCCGTCAT CCATCACGGC AGCGCGGGCA CGGAACACGT GGCCACGCGG 960
GCGGGCGTCC CCAGCTCGT GATCCCCCGG AACACCGACC AGCCGTACTT CGCCGCCAGG 1020
GTTGCCGATC TGGG-

GATCGG TGTGGCGCAC GACGGCCCGA CGC-
CGACCTT CGAGTCCCTG 1080 TCGGCCGCGC
TCACCACGGT CCTGGCGCCG GAAACGCGCG
CGCGGGCGCG GGCCGTGGCG 1140 GCCATG-
GCCC AGACCGACGG CGCGGCGGCG GCCGCG-
GATC TGGTGCTCGC CGCCGTCGGC 1200
GGGAACGAGC CCGCCGTTCC CGCG 1224 which
is SEQ ID NO:1;

(b) AUGCGUGUGU UGTUUGUCGG GUGCGGAACC
CGCGGGGACG UCGAGAUCGC GGUGUCGCUG
60 GCGGUCCGGC UGAAGGCGCU
CGGCGUCGGG ACGCGGAUGU GCGCACCGCC
CGCCGCCGCC 120 GAGCGGCUGG CCGAG-
GUCGA GGUGCCGCAU GUGCCGGUCG GCCU-
UCCGCA GCACAUGAUG 180 UUGCAGGAGG
GGAUGCCGCC GCCGCCCCG GAGGAGGAGC
GGCGGCUCGC GGCCAUGACG 240 GUC-
GAGAUGC AGUUCGACGC GAUCCLCUCG
GCCGCCGAAG GAtGCGUGGC GGUGGUGGCG
300 GUCGGCGAUC UGGCCGCCGC GACCG-
GCGUG CGGUCGGUGG CCGAAAAGCU GGGC-
CUCCCC 360 UUCUUCUACU CCGUCCCGAG
CCCGGUCUAC CUGGCUUCCC CGCACUUCCC
GCCOCCCUAU 420 GACGAGCCGA CCAC-
CCCGGG CGUGACCGAC CACCGGACAC
UGUGGGAAGA GCGUGCCCAC 480 CGG-
UUCGCGG AACGGUACGC GGACACGCUC AAC-
CGCCGGC GCGCCGCGAU CGGCCUGCCG 540
CCGGUGGAGG ACGUCUUCGG CUACGGCCAC
GGCGACCGGC CCAUCCUGUC GGCGGACCCG
600 GUCCUCGCCC COCUGCACCC GGACGUC-
CAC GCCGUGCAGA CCGGCGCGUG GAUC-
CUGACC 660 GACGACCGGC CGCUUCCCCC
GGAGCUGGAG GCGUGCCUGG CCGCCGGCCC
ACCGCCGGUG 720 CACGUGGGUU UCG-
GCAGCUC GUCCGGGAAG GGGAUCGCCG
ACGCCACGAA GAUCGCGGUC 780 GAG-
GUGAGCC GUGCCCACGG CCGCCGGGUG AUC-
CUCUCCC GAGGGUCCAC CGAUCUGCUC 840
CUGCCCGACG ACCGGGAGGA CUGUUUCGCC
AUCGGCGAGG UGAACUUCCA CGCGCUWUUC
900 CCCCGGCUGG CCGCCGUCAT CCAU-
CACGGC AGCGCGGCCA CGGAACACGU GGC-
CACGCGG 960 GCGGGCGUCC CCCACCUCGU
GAUCCCCGG AACACCGACC AGCCGUACUU
CGCCGCCAGG 1020 GUUGCCGAUC UGGG-
GAUCGG UGUGGCGCAC GACGSCCCGA CGC-
CGACCUU CGAGUCCCUG 1080 UCGGCCGCGC
UCACCACGGU CCUGOCOCCG GAAACGCGCG
CGCGGGCGCG GGCCGUGGCG 1140 GCCAUG-
GCCC AGACCGACGG CGCGGCGGCG GCCGCG-
GAUC UGGUGCUCGC CGCCGUCGGC 1200
GGGAACGAGC CCGCCGUUCC CGCG 1224
which is SEQ ID NO:3;

(c) a nucleic acid compound complementary to (a) or (b).

3. An isolated nucleic acid compound of claim 2 herein the sequence of said compound is SEQ ID NO:1 or a sequence complementary to SEQ ID NO:1.

4. An isolated nucleic acid compound of claim 2 wherein the sequence of said compound is SEQ ID NO:3 or a sequence complementary to SEQ ID NO:3.

5. A vector comprising an isolated nucleic acid compound of claim 2.

6. A vector, as in claim 5, wherein said isolated nucleic acid compound is DNA operably linked to a promoter sequence.

7. A host cell containing the vector of claim 5.

8. A host cell containing the vector of claim 6.

9. A method for constructing a recombinant host cell having the potential to express SEQ ID NO:2, said method comprising introducing into said host cell by any suitable means a vector of claim 6.

10. A method for expressing SEQ ID NO:2 in the recombinant host cell of claim 9, said method comprising culturing said recombinant host cell under conditions suitable for gene expression.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 1224 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 1..1224

( x i ) SEQUENCE DESCRIPTION: SEQ ID NO:1:

```
ATG CGT GTG TTG TTG TCG GTG TGC GGA ACC CGC GGG GAC GTC GAG ATC        48
Met Arg Val Leu Leu Ser Val Cys Gly Thr Arg Gly Asp Val Glu Ile
 1               5                  10                  15

GCG GTG TCG CTG GCG GTC CGG CTG AAG GCG CTC GGC GTC GGG ACG CGG        96
Ala Val Ser Leu Ala Val Arg Leu Lys Ala Leu Gly Val Gly Thr Arg
                20                  25                  30

ATG TGC GCA CCG CCC GCC GCC GCC GAG CGG CTG GCC GAG GTC GAG GTG       144
Met Cys Ala Pro Pro Ala Ala Ala Glu Arg Leu Ala Glu Val Glu Val
             35                  40                  45

CCG CAT GTG CCG GTC GGC CTT CCG CAG CAC ATG ATG TTG CAG GAG GGG       192
Pro His Val Pro Val Gly Leu Pro Gln His Met Met Leu Gln Glu Gly
     50                  55                  60

ATG CCG CCG CCG CCC CCG GAG GAG GAG CGG CGG CTC GCG GCC ATG ACG       240
Met Pro Pro Pro Pro Pro Glu Glu Glu Arg Arg Leu Ala Ala Met Thr
 65                  70                  75                  80

GTC GAG ATG CAG TTC GAC GCG ATC CCC TCG GCC GCC GAA GGA TGC GTG       288
Val Glu Met Gln Phe Asp Ala Ile Pro Ser Ala Ala Glu Gly Cys Val
                 85                  90                  95

GCG GTG GTG GCG GTC GGC GAT CTG GCC GCC GCG ACC GGC GTG CGG TCG       336
Ala Val Val Ala Val Gly Asp Leu Ala Ala Ala Thr Gly Val Arg Ser
                100                 105                 110

GTG GCC GAA AAG CTG GGC CTC CCC TTC TTC TAC TCC GTC CCG AGC CCG       384
Val Ala Glu Lys Leu Gly Leu Pro Phe Phe Tyr Ser Val Pro Ser Pro
            115                 120                 125

GTC TAC CTG GCT TCC CCG CAC TTC CCG CCG CCC TAT GAC GAG CCG ACC       432
Val Tyr Leu Ala Ser Pro His Phe Pro Pro Pro Tyr Asp Glu Pro Thr
        130                 135                 140

ACC CCG GGC GTG ACC GAC CAC CGG ACA CTG TGG GAA GAG CGT GCC CAC       480
Thr Pro Gly Val Thr Asp His Arg Thr Leu Trp Glu Glu Arg Ala His
145                 150                 155                 160

CGG TTC GCG GAA CGG TAC GGG GAG ACG CTC AAC CGG CGG CGG GCC GCG       528
Arg Phe Ala Glu Arg Tyr Gly Glu Thr Leu Asn Arg Arg Arg Ala Ala
```

| | | | | | | | | | | | | | | | | |
|---|---|---|---|---|---|---|---|---|---|---|---|---|---|---|---|---|
| | | | | 165 | | | | | 170 | | | | | 175 | | |
| ATC | GGC | CTG | CCG | CCG | GTG | GAG | GAC | GTC | TTC | GGC | TAC | GGC | CAC | GGC | GAC | 576 |
| Ile | Gly | Leu | Pro<br>180 | Pro | Val | Glu | Asp | Val<br>185 | Phe | Gly | Tyr | Gly | His<br>190 | Gly | Asp | |
| CGG | CCC | ATC | CTG | TCG | GCG | GAC | CCG | GTC | CTC | GCC | CCG | CTG | CAG | CCG | GAC | 624 |
| Arg | Pro | Ile<br>195 | Leu | Ser | Ala | Asp | Pro<br>200 | Val | Leu | Ala | Pro | Leu<br>205 | Gln | Pro | Asp | |
| GTC | GAC | GCC | GTG | CAG | ACC | GGC | GCG | TGG | ATC | CTG | ACC | GAC | GAC | CGG | CCG | 672 |
| Val | Asp<br>210 | Ala | Val | Gln | Thr | Gly<br>215 | Ala | Trp | Ile | Leu | Thr<br>220 | Asp | Asp | Arg | Pro | |
| CTT | CCC | CCG | GAG | CTG | GAG | GCG | TTC | CTG | GCC | GCC | GGC | CCA | CCG | CCG | GTG | 720 |
| Leu<br>225 | Pro | Pro | Glu | Leu | Glu<br>230 | Ala | Phe | Leu | Ala | Ala<br>235 | Gly | Pro | Pro | Pro | Val<br>240 | |
| CAC | GTG | GGT | TTC | GGC | AGC | TCG | TCC | GGG | AAG | GGG | ATC | GCC | GAC | GCC | GCG | 768 |
| His | Val | Gly | Phe | Gly<br>245 | Ser | Ser | Ser | Gly | Lys<br>250 | Gly | Ile | Ala | Asp<br>255 | Ala | Ala | |
| AAG | ATC | GCC | GTC | GAG | GTG | AGC | CGT | GCC | CAC | GGC | CGC | CGG | GTG | ATC | CTC | 816 |
| Lys | Ile | Ala | Val<br>260 | Glu | Val | Ser | Arg | Ala<br>265 | His | Gly | Arg | Arg | Val<br>270 | Ile | Leu | |
| TCC | CGA | GGG | TGG | ACC | GAT | CTG | CTC | CTG | CCC | GAC | GAC | CGG | GAG | GAC | TGT | 864 |
| Ser | Arg | Gly<br>275 | Trp | Thr | Asp | Leu | Leu<br>280 | Leu | Pro | Asp | Asp | Arg<br>285 | Glu | Asp | Cys | |
| TTC | GCC | ATC | GGC | GAG | GTG | AAC | TTC | CAG | GCG | CTG | TTC | CCC | CGG | GTG | GCC | 912 |
| Phe | Ala<br>290 | Ile | Gly | Glu | Val | Asn<br>295 | Phe | Gln | Ala | Leu | Phe<br>300 | Pro | Arg | Val | Ala | |
| GCC | GTC | ATC | CAT | CAC | GGC | AGC | GCG | GGC | ACG | GAA | CAC | GTG | GCC | ACG | CGG | 960 |
| Ala | Val | Ile | His | His<br>310 | Gly | Ser | Ala | Gly | Thr<br>315 | Glu | His | Val | Ala | Thr<br>320 | Arg | |
| Ala<br>305 | | | | | | | | | | | | | | | | |
| GCG | GGC | GTC | CCC | CAG | CTC | GTG | ATC | CCC | CGG | AAC | ACC | GAC | CAG | CCG | TAC | 1008 |
| Ala | Gly | Val | Pro | Gln<br>325 | Leu | Val | Ile | Pro | Arg<br>330 | Asn | Thr | Asp | Gln | Pro<br>335 | Tyr | |
| TTC | GCC | GCC | AGG | GTT | GCC | GAT | CTG | GGG | ATC | GGT | GTG | GCG | CAC | GAC | GGC | 1056 |
| Phe | Ala | Ala | Arg<br>340 | Val | Ala | Asp | Leu | Gly<br>345 | Ile | Gly | Val | Ala | His<br>350 | Asp | Gly | |
| CCG | ACG | CCG | ACC | TTC | GAG | TCC | CTG | TCG | GCC | GCG | CTC | ACC | ACG | GTC | CTG | 1104 |
| Pro | Thr | Pro<br>355 | Thr | Phe | Glu | Ser | Leu<br>360 | Ser | Ala | Ala | Leu | Thr<br>365 | Thr | Val | Leu | |
| GCG | CCG | GAA | ACG | CGC | GCG | CGG | GCG | CGG | GCC | GTG | GCG | GCC | ATG | GCC | CAG | 1152 |
| Ala | Pro<br>370 | Glu | Thr | Arg | Ala | Arg<br>375 | Ala | Arg | Ala | Val | Ala<br>380 | Ala | Met | Ala | Gln | |
| ACC | GAC | GGC | GCG | GCG | GCG | GCC | GCG | GAT | CTG | GTG | CTC | GCC | GCC | GTC | GGC | 1200 |
| Thr | Asp | Gly | Ala | Ala<br>390 | Ala | Ala | Ala | Asp | Leu<br>395 | Val | Leu | Ala | Ala | Val<br>400 | Gly | |
| Asp<br>385 | | | | | | | | | | | | | | | | |
| GGG | AAC | GAG | CCC | GCC | GTT | CCC | GCG | | | | | | | | | 1224 |
| Gly | Asn | Glu | Pro | Ala<br>405 | Val | Pro | Ala | | | | | | | | | |

( 2 ) INFORMATION FOR SEQ ID NO:2:

( i ) SEQUENCE CHARACTERISTICS:
        ( A ) LENGTH: 408 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met<br>1 | Arg | Val | Leu | Leu<br>5 | Ser | Val | Cys | Gly | Thr<br>10 | Arg | Gly | Asp | Val | Glu | Ile<br>15 |
| Ala | Val | Ser | Leu<br>20 | Ala | Val | Arg | Leu | Lys<br>25 | Ala | Leu | Gly | Val | Gly<br>30 | Thr | Arg |

| Met | Cys | Ala | Pro | Pro | Ala | Ala | Ala | Glu | Arg | Leu | Ala | Glu | Val | Glu | Val |
| | | 35 | | | | 40 | | | | | 45 | | | | |
| Pro | His | Val | Pro | Val | Gly | Leu | Pro | Gln | His | Met | Met | Leu | Gln | Glu | Gly |
| | 50 | | | | 55 | | | | | 60 | | | | | |
| Met | Pro | Pro | Pro | Pro | Pro | Glu | Glu | Glu | Arg | Arg | Leu | Ala | Ala | Met | Thr |
| 65 | | | | | 70 | | | | | 75 | | | | | 80 |
| Val | Glu | Met | Gln | Phe | Asp | Ala | Ile | Pro | Ser | Ala | Ala | Glu | Gly | Cys | Val |
| | | | | 85 | | | | | 90 | | | | | 95 | |
| Ala | Val | Val | Ala | Val | Gly | Asp | Leu | Ala | Ala | Ala | Thr | Gly | Val | Arg | Ser |
| | | | | 100 | | | | | 105 | | | | 110 | | |
| Val | Ala | Glu | Lys | Leu | Gly | Leu | Pro | Phe | Phe | Tyr | Ser | Val | Pro | Ser | Pro |
| | | | 115 | | | | 120 | | | | | 125 | | | |
| Val | Tyr | Leu | Ala | Ser | Pro | His | Phe | Pro | Pro | Pro | Tyr | Asp | Glu | Pro | Thr |
| | | 130 | | | | 135 | | | | | 140 | | | | |
| Thr | Pro | Gly | Val | Thr | Asp | His | Arg | Thr | Leu | Trp | Glu | Glu | Arg | Ala | His |
| 145 | | | | | 150 | | | | | 155 | | | | | 160 |
| Arg | Phe | Ala | Glu | Arg | Tyr | Gly | Glu | Thr | Leu | Asn | Arg | Arg | Ala | Ala | |
| | | | | 165 | | | | | 170 | | | | 175 | | |
| Ile | Gly | Leu | Pro | Pro | Val | Glu | Asp | Val | Phe | Gly | Tyr | Gly | His | Gly | Asp |
| | | | 180 | | | | | 185 | | | | | 190 | | |
| Arg | Pro | Ile | Leu | Ser | Ala | Asp | Pro | Val | Leu | Ala | Pro | Leu | Gln | Pro | Asp |
| | | 195 | | | | | 200 | | | | | 205 | | | |
| Val | Asp | Ala | Val | Gln | Thr | Gly | Ala | Trp | Ile | Leu | Thr | Asp | Asp | Arg | Pro |
| | 210 | | | | | 215 | | | | | 220 | | | | |
| Leu | Pro | Pro | Glu | Leu | Glu | Ala | Phe | Leu | Ala | Ala | Gly | Pro | Pro | Pro | Val |
| 225 | | | | | 230 | | | | | 235 | | | | | 240 |
| His | Val | Gly | Phe | Gly | Ser | Ser | Ser | Gly | Lys | Gly | Ile | Ala | Asp | Ala | Ala |
| | | | | 245 | | | | | 250 | | | | | 255 | |
| Lys | Ile | Ala | Val | Glu | Val | Ser | Arg | Ala | His | Gly | Arg | Arg | Val | Ile | Leu |
| | | | 260 | | | | | 265 | | | | 270 | | | |
| Ser | Arg | Gly | Trp | Thr | Asp | Leu | Leu | Leu | Pro | Asp | Asp | Arg | Glu | Asp | Cys |
| | | 275 | | | | | 280 | | | | | 285 | | | |
| Phe | Ala | Ile | Gly | Glu | Val | Asn | Phe | Gln | Ala | Leu | Phe | Pro | Arg | Val | Ala |
| | 290 | | | | | 295 | | | | | 300 | | | | |
| Ala | Val | Ile | His | His | Gly | Ser | Ala | Gly | Thr | Glu | His | Val | Ala | Thr | Arg |
| 305 | | | | | 310 | | | | | 315 | | | | | 320 |
| Ala | Gly | Val | Pro | Gln | Leu | Val | Ile | Pro | Arg | Asn | Thr | Asp | Gln | Pro | Tyr |
| | | | | 325 | | | | | 330 | | | | | 335 | |
| Phe | Ala | Ala | Arg | Val | Ala | Asp | Leu | Gly | Ile | Gly | Val | Ala | His | Asp | Gly |
| | | | 340 | | | | | 345 | | | | | 350 | | |
| Pro | Thr | Pro | Thr | Phe | Glu | Ser | Leu | Ser | Ala | Ala | Leu | Thr | Thr | Val | Leu |
| | | 355 | | | | | 360 | | | | | 365 | | | |
| Ala | Pro | Glu | Thr | Arg | Ala | Arg | Ala | Arg | Ala | Val | Ala | Ala | Met | Ala | Gln |
| | 370 | | | | | 375 | | | | | 380 | | | | |
| Thr | Asp | Gly | Ala | Ala | Ala | Ala | Ala | Asp | Leu | Val | Leu | Ala | Ala | Val | Gly |
| 385 | | | | | 390 | | | | | 395 | | | | | 400 |
| Gly | Asn | Glu | Pro | Ala | Val | Pro | Ala | | | | | | | | |
| | | | | 405 | | | | | | | | | | | |

( 2 ) INFORMATION FOR SEQ ID NO:3:

( i ) SEQUENCE CHARACTERISTICS:
        ( A ) LENGTH: 1224 base pairs
        ( B ) TYPE: nucleic acid
        ( C ) STRANDEDNESS: single
        ( D ) TOPOLOGY: linear -continued (ii) MOLECULE TYPE: mRNA (iii) HYPOTHETICAL: NO (iv) ANTI-SENSE: NO (xi) SEQUENCE DESCRIPTION: SEQ ID NO:3:

| AUGCGUGUGU | UGUUGUCGGU | GUGCGGAACC | CGCGGGGACG | UCGAGAUCGC | GGUGUCGCUG | 60 |
| GCGGUCCGGC | UGAAGGCGCU | CGGCGUCGGG | ACGCGGAUGU | GCGCACCGCC | CGCCGCCGCC | 120 |
| GAGCGGCUGG | CCGAGGUCGA | GGUGCCGCAU | GUGCCGGUCG | GCCUUCCGCA | GCACAUGAUG | 180 |
| UUGCAGGAGG | GGAUGCCGCC | GCCGCCCCCG | GAGGAGGAGC | GGCGGCUCGC | GGCCAUGACG | 240 |
| GUCGAGAUGC | AGUUCGACGC | GAUCCCCUCG | GCCGCCGAAG | GAUGCGUGGC | GGUGGUGGCG | 300 |
| GUCGGCGAUC | UGGCCGCCGC | GACCGGCGUG | CGGUCGGUGG | CCGAAAAGCU | GGGCCUCCCC | 360 |
| UUCUUCUACU | CCGUCCCGAG | CCCGGUCUAC | CUGGCUUCCC | CGCACUUCCC | GCCGCCCUAU | 420 |
| GACGAGCCGA | CCACCCCGGG | CGUGACCGAC | CACCGGACAC | UGUGGGAAGA | GCGUGCCCAC | 480 |
| CGGUUCGCGG | AACGGUACGG | GGAGACGCUC | AACCGGCGGC | GGGCCGCGAU | CGGCCUGCCG | 540 |
| CCGGUGGAGG | ACGUCUUCGG | CUACGGCCAC | GGCGACCGGC | CCAUCCUGUC | GGCGGACCCG | 600 |
| GUCCUCGCCC | CGCUGCAGCC | GGACGUCGAC | GCCGUGCAGA | CCGGCGCGUG | GAUCCUGACC | 660 |
| GACGACCGGC | CGCUUCCCCC | GGAGCUGGAG | GCGUUCCUGG | CCGCCGGCCC | ACCGCCGGUG | 720 |
| CACGUGGGUU | UCGGCAGCUC | GUCCGGGAAG | GGGAUCGCCG | ACGCCGCGAA | GAUCGCCGUC | 780 |
| GAGGUGAGCC | GUGCCCACGG | CCGCCGGGUG | AUCCUCUCCC | GAGGGUGGAC | CGAUCUGCUC | 840 |
| CUGCCCGACG | ACCGGGAGGA | CUGUUUCGCC | AUCGGCGAGG | UGAACUUCCA | GGCGCUGUUC | 900 |
| CCCCGGGUGG | CCGCCGUCAU | CCAUCACGGC | AGCGCGGGCA | CGGAACACGU | GGCCACGCGG | 960 |
| GCGGGCGUCC | CCCAGCUCGU | GAUCCCCCGG | AACACCGACC | AGCCGUACUU | CGCCGCCAGG | 1020 |
| GUUGCCGAUC | UGGGGAUCGG | UGUGGCGCAC | GACGGCCCGA | CGCCGACCUU | CGAGUCCCUG | 1080 |
| UCGGCCGCGC | UCACCACGGU | CCUGGCGCCG | GAAACGCGCG | CGCGGGCGCG | GCCGUGGCG | 1140 |
| GCCAUGGCCC | AGACCGACGG | CGCGGCGGCG | GCCGCGGAUC | UGGUGCUCGC | CGCCGUCGGC | 1200 |
| GGGAACGAGC | CCGCCGUUCC | CGCG | | | | 1224 |